United States Patent
Hong et al.

(10) Patent No.: US 9,937,480 B2
(45) Date of Patent: Apr. 10, 2018

(54) PURIFICATION APPARATUS INCLUDING CONTINUOUS REACTORS AND PURIFICATION METHOD USING CONTINUOUS REACTORS

(71) Applicant: LAMINAR CO.,LTD, Seongnam-si, Gyeonggi-do (KR)

(72) Inventors: Jong Pal Hong, Seoul (KR); Chil Won Lee, Seongnam-si (KR); Hee Wan Lee, Seongnam-si (KR); Gyeong Rye Choi, Seongnam-si (KR)

(73) Assignee: LAMINAR CO., LTD, Seongnam-Si (KR)

( * ) Notice: Subject to any disclaimer, the term of this patent is extended or adjusted under 35 U.S.C. 154(b) by 421 days.

(21) Appl. No.: 14/635,925

(22) Filed: Mar. 2, 2015

(65) Prior Publication Data

US 2015/0196890 A1    Jul. 16, 2015

Related U.S. Application Data

(63) Continuation of application No. PCT/KR2013/007885, filed on Sep. 2, 2013.

(30) Foreign Application Priority Data

Sep. 3, 2012 (KR) .................. 10-2012-0097027
Sep. 27, 2012 (KR) .................. 10-2012-0107996

(51) Int. Cl.
| | | |
|---|---|---|
| *B01D 9/00* | (2006.01) | |
| *B01D 36/00* | (2006.01) | |
| *B01J 19/18* | (2006.01) | |
| *C07D 209/20* | (2006.01) | |
| *B01J 19/10* | (2006.01) | |
| *B01J 19/00* | (2006.01) | |
| *C07D 209/16* | (2006.01) | |

(52) U.S. Cl.
CPC ............. *B01J 19/10* (2013.01); *B01D 9/00* (2013.01); *B01D 9/0054* (2013.01);
(Continued)

(58) Field of Classification Search
CPC ........ B01J 19/10; B01J 19/0013; B01J 19/18; B01J 2219/00103; B01J 2219/00033; B01J 2219/00094; B01J 2219/00051; B01J 2219/00054; B01J 2219/00058; B01J 2219/0053; B01J 2219/0033; B01J 2219/02; B01J 2219/0204; B01J 2219/0236; B01J 2219/0869; B01J 2219/18; B01D 9/0054; B01D 36/00; B01D 9/0063; B01D 9/0081; B01D 9/00; B01D 9/008; B01D 17/0217; B01D 17/12; B01D 21/26; B01D 21/262; B01D 39/02;
(Continued)

(56) References Cited

U.S. PATENT DOCUMENTS 2,725,219 A * 11/1955 Firth ................. B01J 19/10
                                                        241/1
3,004,013 A * 10/1961 Kirz .................. B01J 19/1862
                                                        422/225
(Continued)

*Primary Examiner* — Joseph Drodge
(74) *Attorney, Agent, or Firm* — Im IP Law; C. Andrew Im

(57) ABSTRACT

A purification apparatus and a purification method using the purification apparatus. A solution stored in a solution storage tank is diffused/agitated with an ultrasonic wave. An air compressor transfers the solution to a reactor. The solution is mixed in the reactor with a solvent fed through another passage to produce a reactant.

13 Claims, 12 Drawing Sheets

(52) U.S. Cl.
CPC ......... *B01D 9/0063* (2013.01); *B01D 9/0081* (2013.01); *B01D 36/00* (2013.01); *B01J 19/0013* (2013.01); *B01J 19/18* (2013.01); *C07D 209/16* (2013.01); *C07D 209/20* (2013.01); *B01D 2009/0095* (2013.01); *B01J 2219/00033* (2013.01); *B01J 2219/00094* (2013.01); *B01J 2219/00103* (2013.01)

(58) Field of Classification Search
CPC ........ B01D 39/06; B01D 9/0059; B01D 9/02; B01D 2009/0086; B01D 36/04; C07D 209/16; C07D 209/20
USPC ....... 210/149, 173, 175, 182, 184, 200–203, 210/258, 259, 511, 512.1, 282; 422/128, 422/224–226, 285, 286, 616; 366/108, 366/144, 145, 149, 154.1, 154.2, 348; 548/497
See application file for complete search history.

(56) References Cited

U.S. PATENT DOCUMENTS

| | | | | |
|---|---|---|---|---|
| 4,456,735 A * | 6/1984 | Engelmann | ............. | C08F 14/06 525/317 |
| 5,843,386 A * | 12/1998 | Makino | ...................... | B01J 3/04 210/177 |
| 6,306,658 B1 * | 10/2001 | Turner | ............. | B01F 15/00207 374/E13.001 |
| 2005/0074380 A1 * | 4/2005 | Boren | ................... | B01J 19/006 423/1 |
| 2005/0260106 A1 * | 11/2005 | Marhasin | ............. | B01F 15/065 422/128 |
| 2010/0124583 A1 * | 5/2010 | Medoff | .................... | A61K 8/97 426/2 |
| 2011/0061289 A1 * | 3/2011 | Mann | ....................... | B01J 4/002 44/308 |
| 2015/0165340 A1 * | 6/2015 | Hong | ................... | B01D 9/0081 548/497 |

* cited by examiner

[Fig.1]
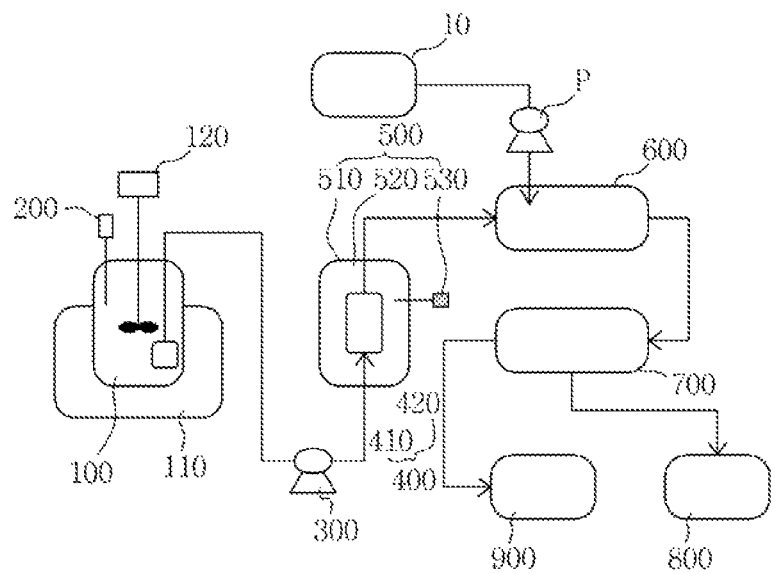
[Fig.2]
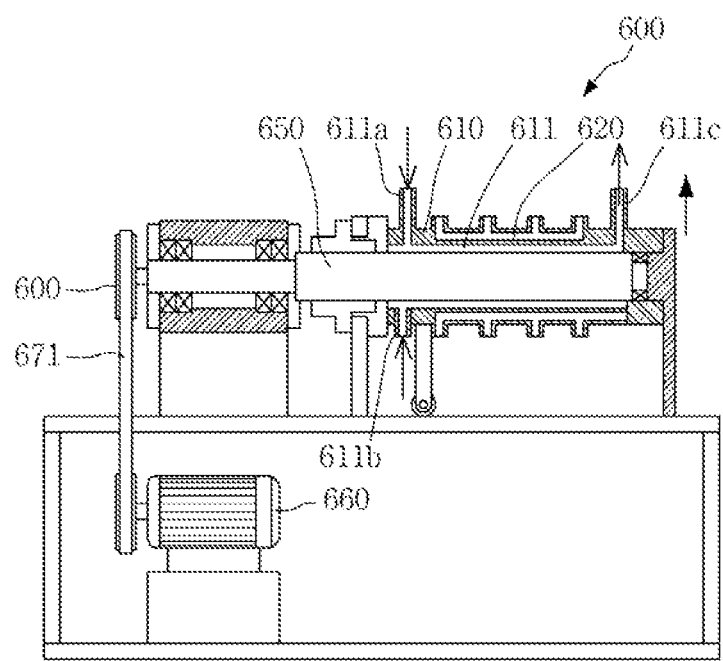

[Fig.3]
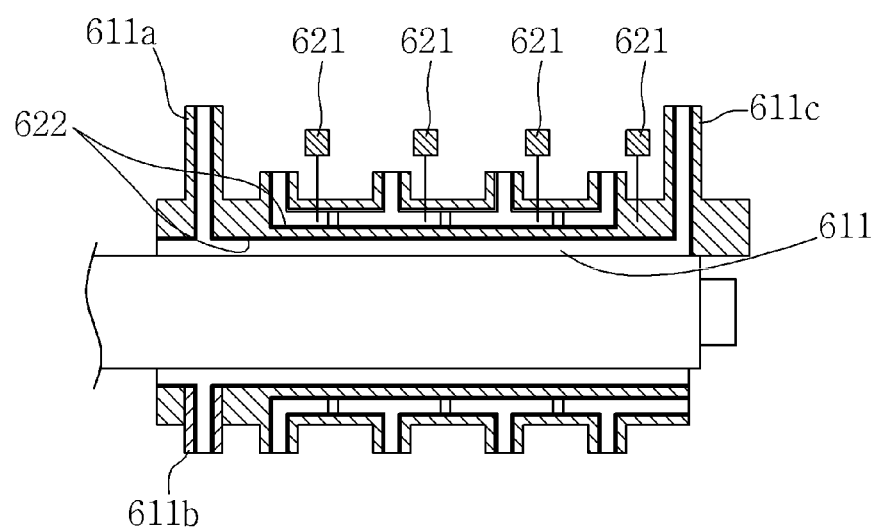

[FIG. 4]
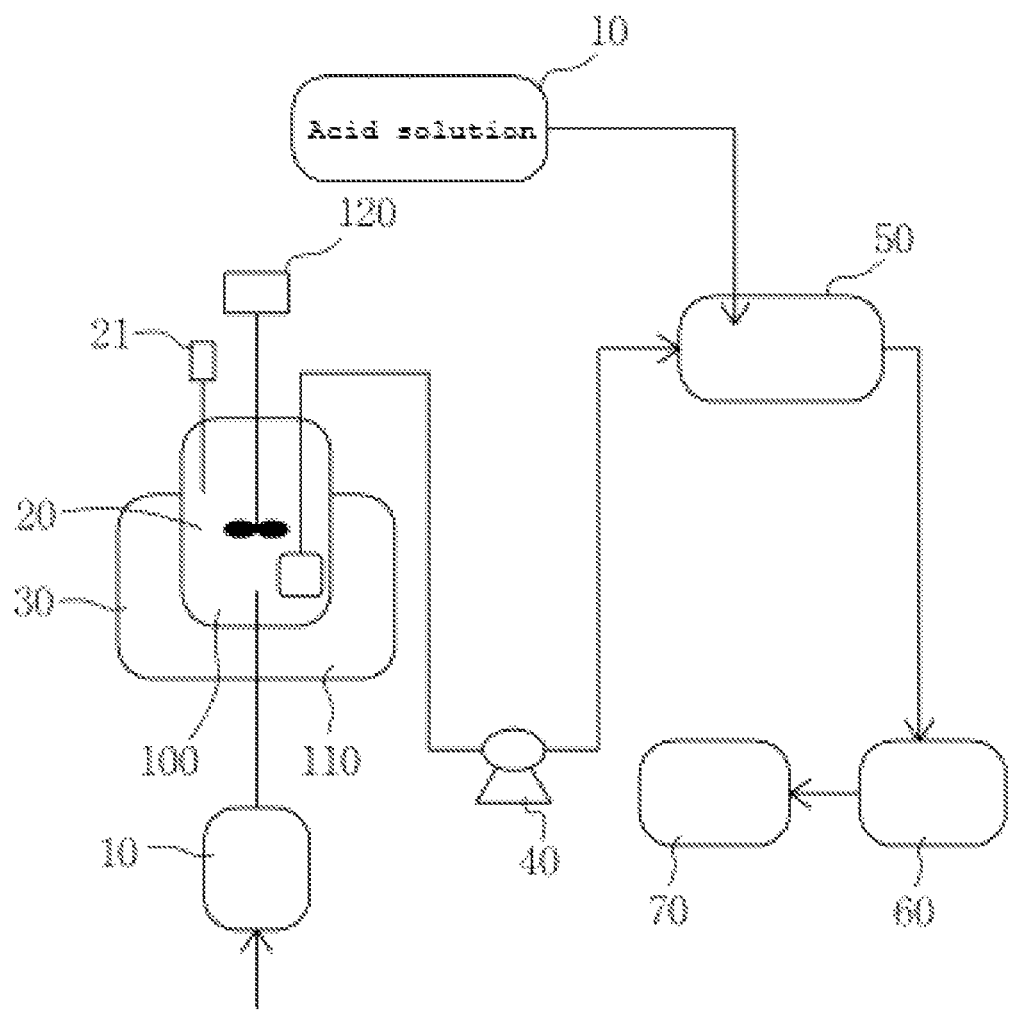

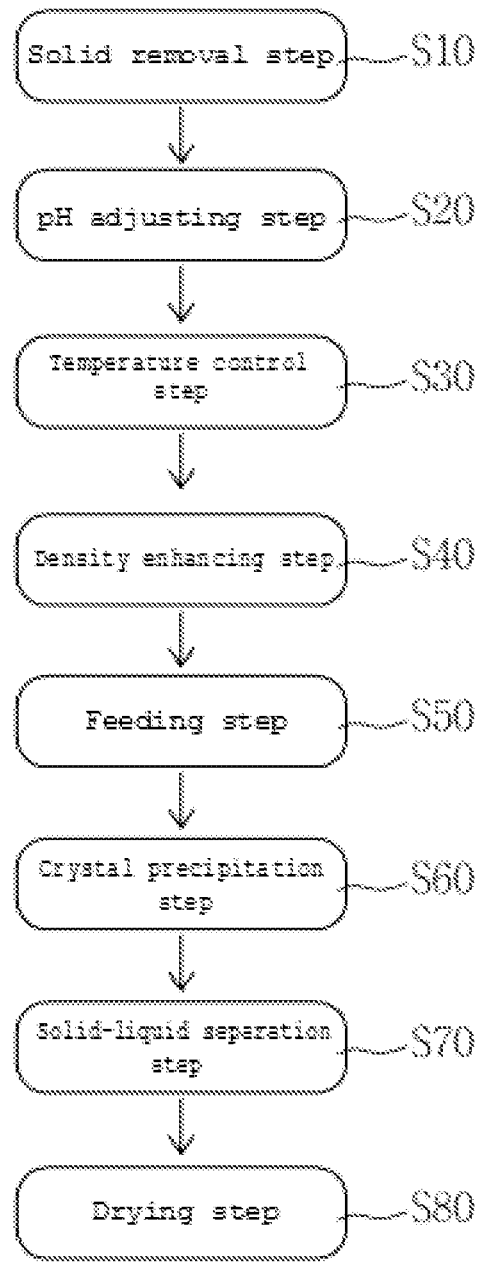
[FIG. 5]

[FIG. 6]
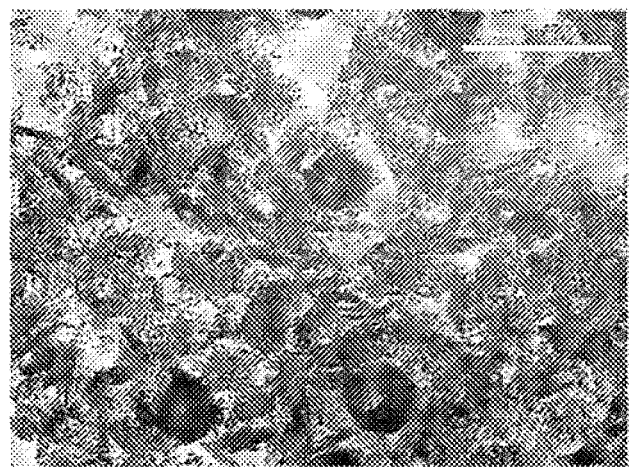
[FIG. 7]
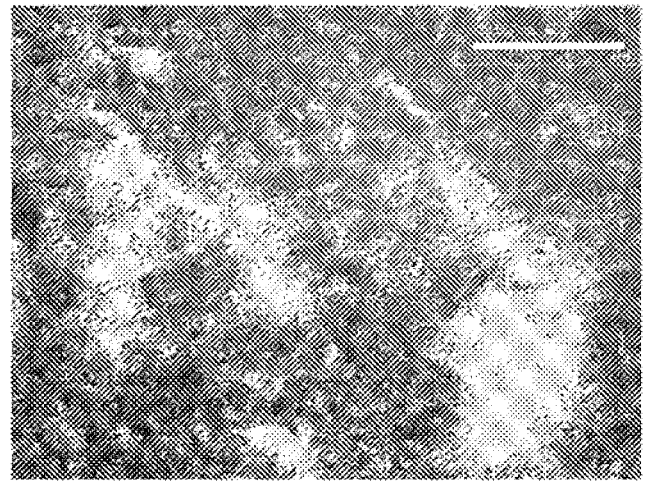

[FIG. 8]
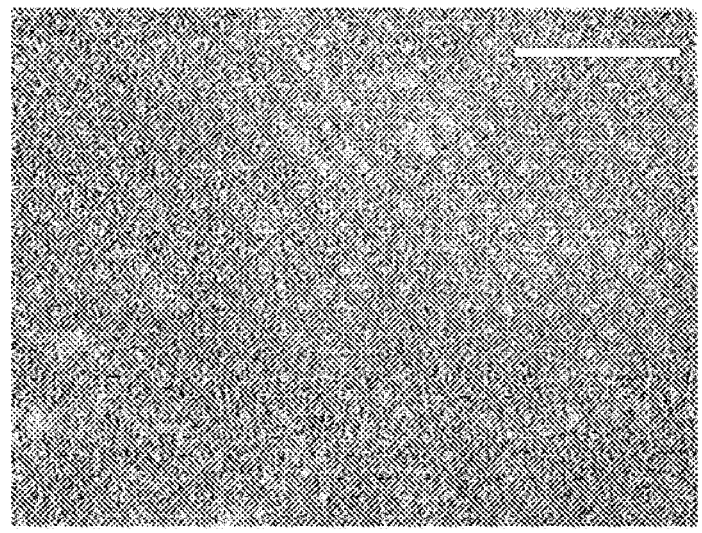
[FIG. 9]
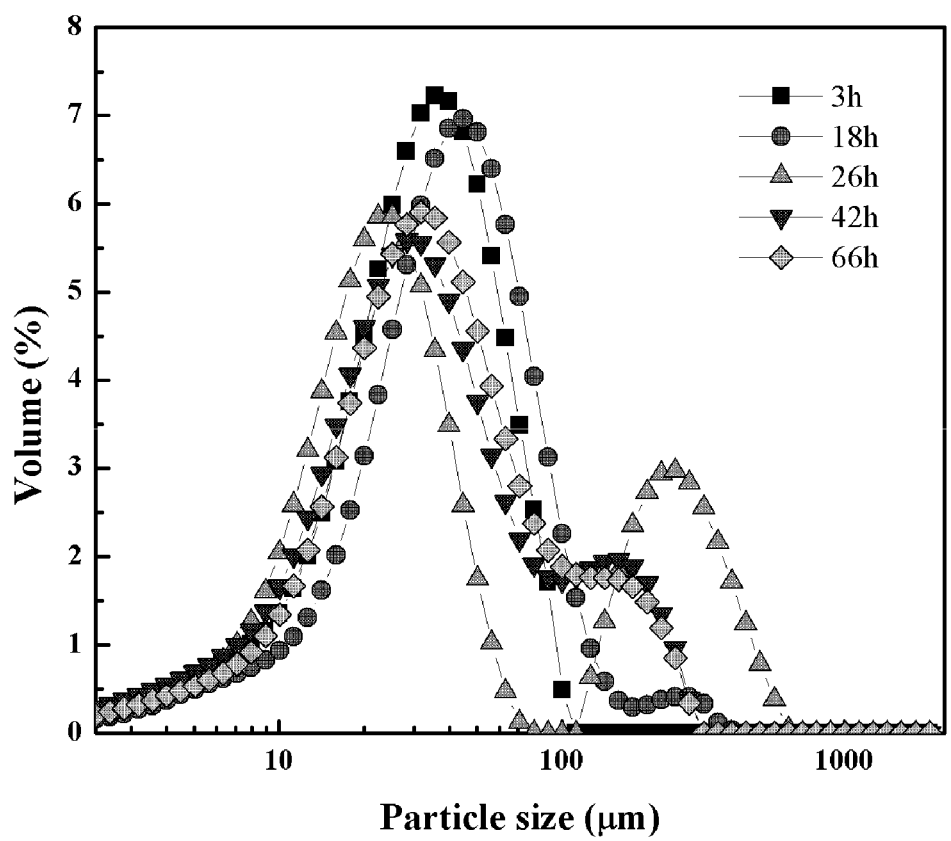

[FIG. 10]
[FIG. 11]
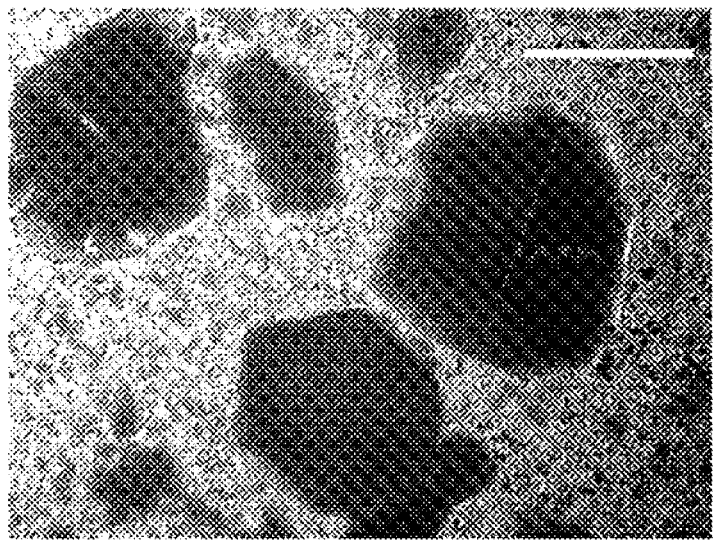

[FIG. 12]
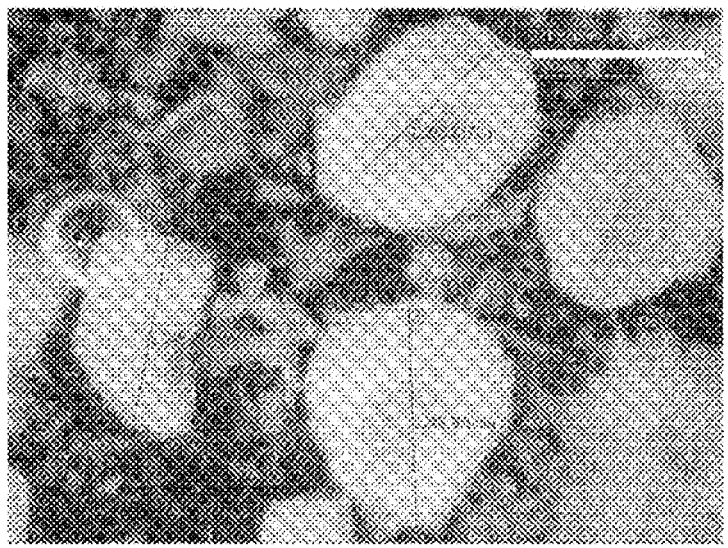
[FIG. 13]
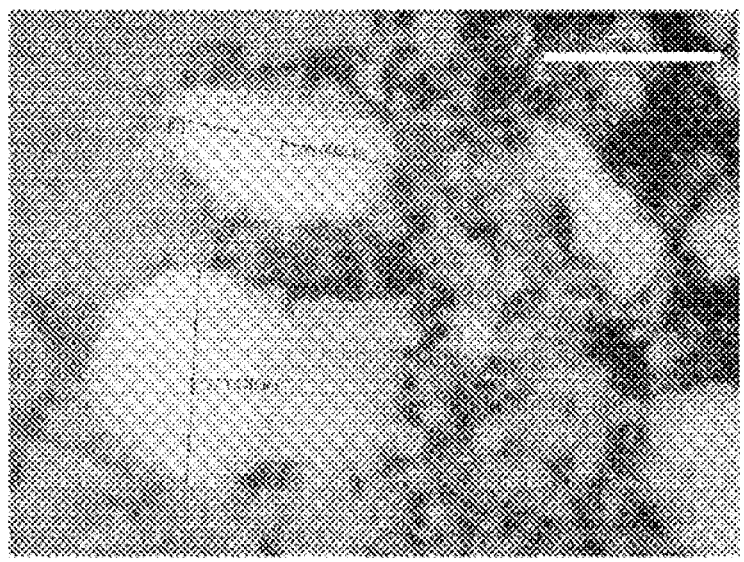

[FIG. 14]
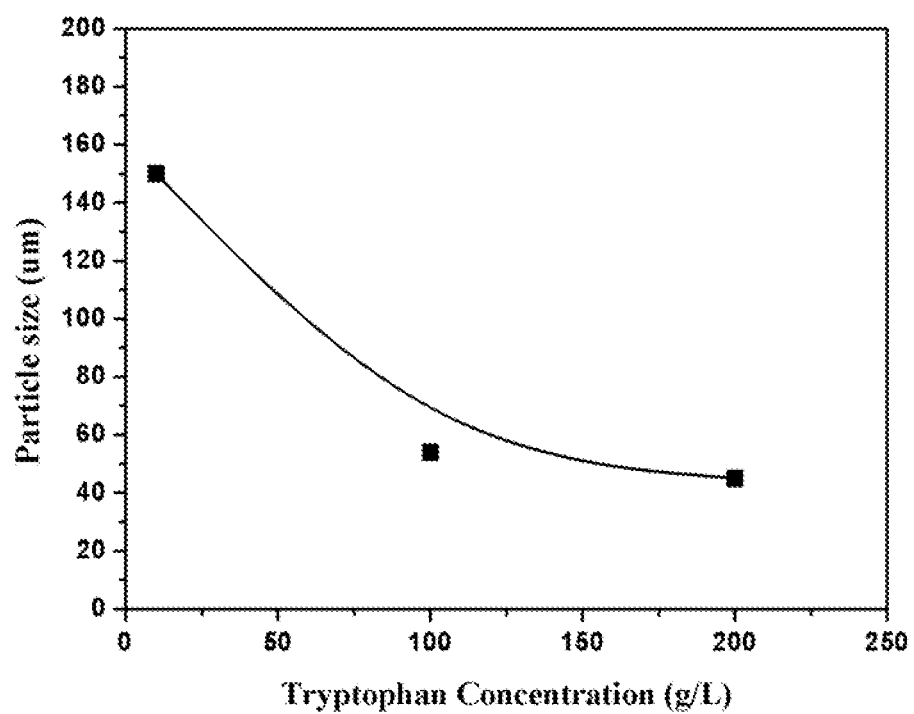

[FIG. 15]
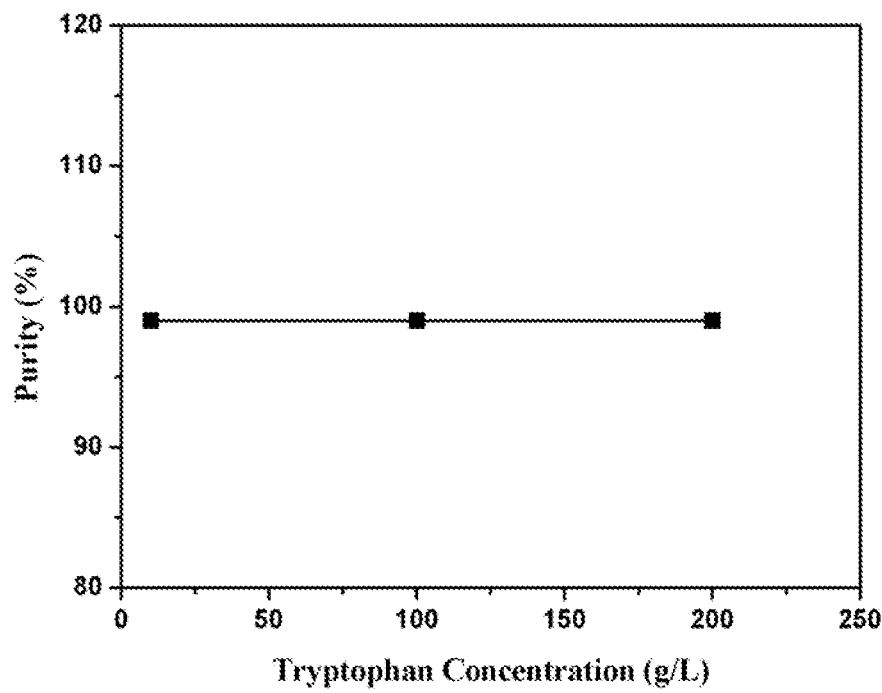
[FIG. 16]
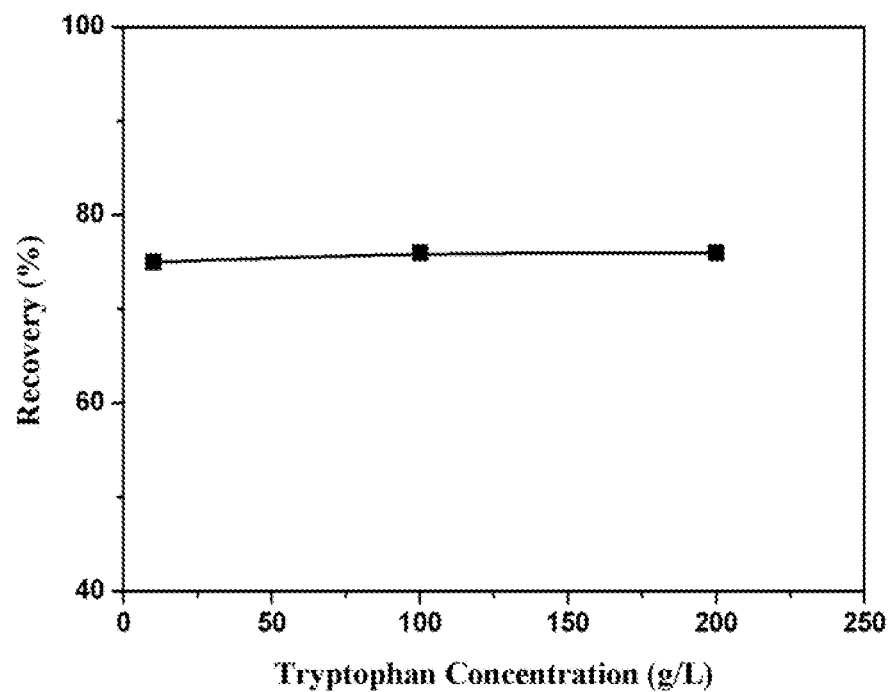

[FIG. 17]
[FIG. 18]
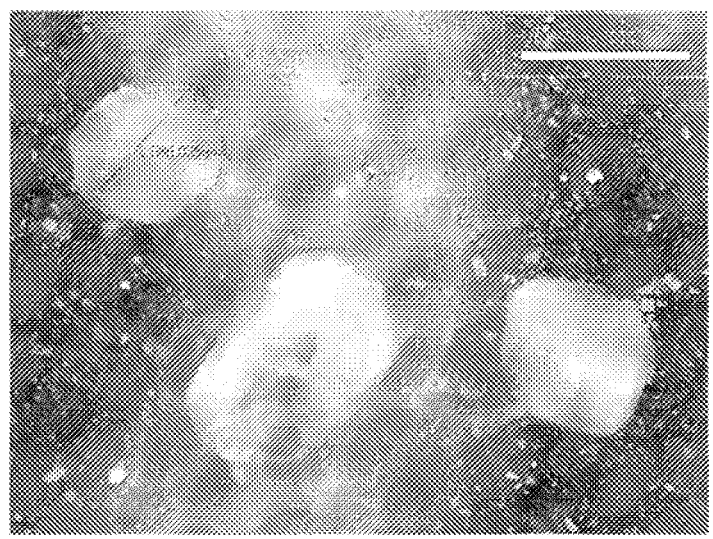

[FIG. 19]
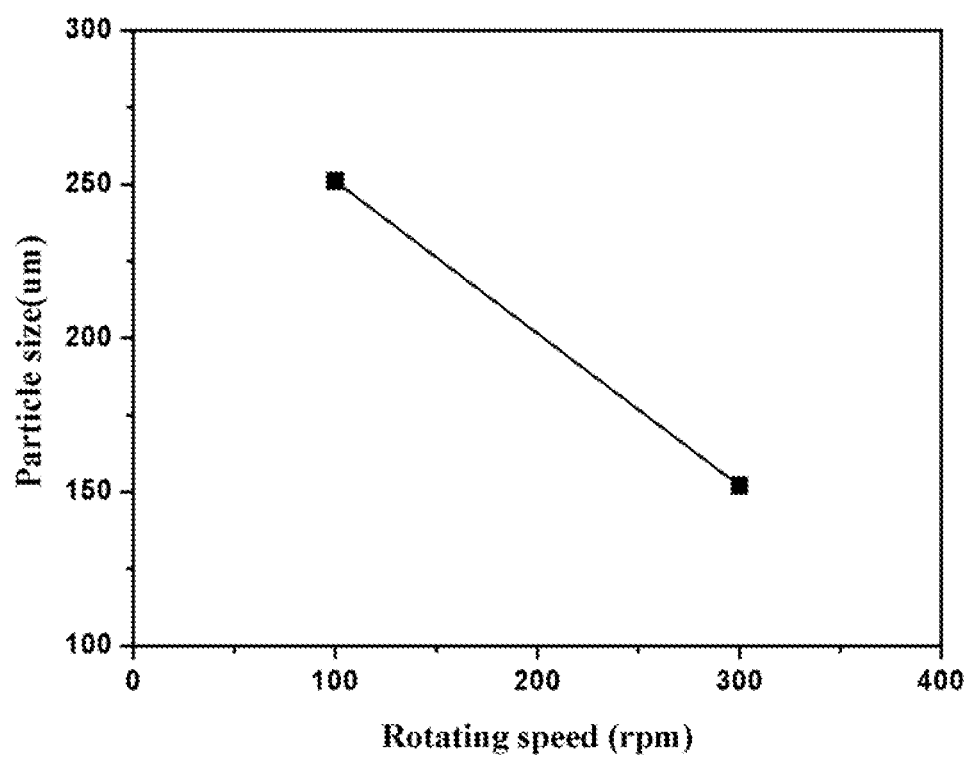

PURIFICATION APPARATUS INCLUDING CONTINUOUS REACTORS AND PURIFICATION METHOD USING CONTINUOUS REACTORS

RELATED APPLICATIONS

This application is a continuation of application No. PCT/KR2013/007885 filed Sep. 2, 2013, which claims priority from Korean Patent Application Nos. 10-2012-0097027 filed Sep. 3, 2012 and 10-2012-0107996 filed Sep. 27, 2012, each of which is herein incorporated by reference in its entirety.

TECHNICAL FIELD

The present invention relates to a purification apparatus including continuous reactors and, more particularly to, a purification apparatus that involves diffusing/agitating a solution stored in a solution storage tank with the ultrasonic wave, transferring the solution to a reactor through an air compressor and then mixing the solution in the reactor with a solvent fed through another passage to produce a reactant, and a purification method using the purification apparatus.

BACKGROUND ART

Generally, many materials need to be purified. Purification is also required to organic materials and essential amino acids used for feedstuff additives, medicines, health foods, etc. For example, organic materials used for organic light-emitting device are obtained by isolating a pure target component from the conventional synthetic substance for the use purpose in thin film deposition. With enhanced purification techniques of the organic materials, the organic light-emitting devices are allowed to improve the light-emitting efficiency and extend the light-emission life span.

For the production of organic materials on a large scale, it is essential to use the purification techniques for organic materials with reduced process time and enhanced purification efficiency.

Tryptophan is one of essential amino acids. The conventional purification techniques for tryptophan are disclosed in Japanese Patent Publication Nos. 126070/1986, 39857/1984 and 126070/1983.

However, the method of using an ultrafiltration membrane according to the technique of Japanese Patent Publication No. 895/1983 cannot eliminate impurities merely at a fixed elimination rate, ending up imposing an overload on the resin and reducing the reuse cycle of the non-polar highly porous resin.

Further, the method specified in Japanese Patent Publication No. 39857/1984 is insufficient in eliminating impurities and makes it difficult to obtain crystals with transmission of 95% or higher.

Furthermore, the method disclosed in Japanese Patent Publication No. 126070/1986 forms the structure of tryptophan including unstable indole rings when heating the reaction solution containing lots of impurities and prepared by the fermentation method up to 95 to 100 C in the presence of active carbon, which increases the formation of decomposed and discolored substances.

OBJECT AND SUMMARY OF THE INVENTION

For solving the problem with the prior art, it is an object of the present invention to provide an ultrahigh purification apparatus including a continuous reactor that has a construction capable of producing an organic material for organic light-emitting device with ultrahigh purity of 99.9% or greater, which purification apparatus involves diffusing/agitating a solution with ultrasonic wave, transferring the solution to the reactor through an air compressor and mixing the solution with a solvent added through another passage in the reactor to produce a reactant.

It is another object of the present invention to provide a tryptophan purification apparatus that adopts a method of dissolving tryptophan in an acid solution or an alkaline solution and then adding the opposite solution (i.e., an alkaline solution or an acid solution) to neutralize the pH value to cause precipitation and uses a continuous reactor to continuously yield the product, increase the production rate three times as fast as the existing methods, enhance recovery rate and purity and increase the density of particles by using a polymer material as an additive, resulting in the higher strength of the product that makes the product not easily broken.

In accordance with one embodiment of the present invention, the present invention provides a purification apparatus including a continuous reactor that includes: a solution storage tank for storing a solution; an ultrasonic diffuser for diffusing particles contained in the solution of the solution storage tank with ultrasonic wave; an agitator for agitating the solution stored in the solution storage tank; a heating jacket provided outside the solution storage tank to control the internal temperature of the solution storage tank; an air compressor for suctioning and transferring the solution of the solution storage tank to the next position; and a reactor for receiving the solution transferred by the air compressor and a solvent transferred through a separate passage and agitating the solution at high speed to continuously produce a reactant having uniform particles.

According to the construction of the present invention, it is possible to produce an organic material used for organic light-emitting device with ultrahigh purity on a large scale. Particularly, the crystallization method according to the present invention can obtain an organic material having an ultrahigh purity of 99.9% or greater.

The organic field-effect light-emitting device made using the organic material can benefit from the use of the organic material of higher purity in terms of reduced dark spot growth, improved electric/optical characteristics of the device and extended lifespan of the device.

Further, relative to the conventional methods, the present invention using a continuous reactor can enhance in the recovery rate of tryptophan by about 10%, enable continuous production with enhanced production rate three times or greater and increase the purity to 99.9% or higher.

Furthermore, the present invention using a polymer material as an additive can enhance the density of particles and thus make the particles not easily broken.

BRIEF DESCRIPTION OF DRAWINGS

FIG. 1 is an illustration showing the construction of an ultrahigh purification apparatus according to the present invention.

FIG. 2 is a detailed illustration showing the construction of a continuous reactor adopted in the purification apparatus according to the present invention.

FIG. 3 is an illustration showing the construction of a cylinder of the continuous reactor in the purification apparatus according to the present invention.

FIG. 4 is an illustration showing the construction of a tryptophan purification apparatus as another embodiment of the purification apparatus according to the present invention.

FIG. 5 is a flow chart showing a tryptophan purification method according to the present invention.

FIGS. 6, 7 and 8 show the change of crystals as a function of the addition rate of sulfuric acid in the tryptophan purification method according to the present invention.

FIG. 9 is a particle size distribution graph in the tryptophan purification method according to the present invention.

FIGS. 10 to 13 show images of the tryptophan crystal shape as a function of the reaction time (1 hour in FIG. 10, 6 hours in FIG. 11, 26 hours in FIG. 12, and 52 hours in FIG. 13) in the tryptophan purification method according to the present invention.

FIG. 14 is a graph showing the change of the particle size as a function of the dissolved tryptophan concentration in the tryptophan purification method according to the present invention.

FIG. 15 is a graph showing the change of the purity as a function of the dissolved tryptophan concentration in the tryptophan purification method according to the present invention.

FIG. 16 is a graph showing the change of the recovery rate as a function of the dissolved tryptophan concentration in the tryptophan purification method according to the present invention.

FIGS. 17 and 18 are images showing the change of the particle shape as a function of the agitation rate in the tryptophan purification method according to the present invention.

FIG. 19 is a graph showing the change of the particle size as a function of the agitation rate in the tryptophan purification method according to the present invention.

DETAILED DESCRIPTION OF EMBODIMENTS

The present invention is a purification apparatus including a reactor that is composed of a solution storage tank, an ultrasonic diffuser, an agitator, a heating jacket, an air compressor, and a reactor, and further optionally includes a filter a separator or a dehydrator, a dryer, etc.

Example 1

The purification apparatus shown in FIGS. 1, 2 and 3 is a purification apparatus including a reactor. The apparatus includes a solution storage tank 100, an ultrasonic diffuser 200, an air compressor 300, a filter cartridge 400, a temperature control device 500, a continuous reactor 600, an organic material separator 700, an organic material storage tank 800, and an analyzer and compensator module 900.

The solution storage tank 100 serves to store a solution containing an organic material (OLED) dissolved in an organic solvent. The concentration of the solution containing the organic material is preferably 100 g/L or less. When the concentration of the solution containing the organic material is above the concentration range, the crystallization reaction is retarded or the desired purity is hard to achieve. In this regard, the organic material refers to any kind of material disposed between positive and negative electrodes of an organic light-emitting device. For example, the organic material or the organic metal material used for organic field-effect light-emitting device may include light-emitting host materials, dopant materials, hole injection-transfer materials, electron injection-transfer materials, hole/electron suppressing layer materials, etc.

The solution storage tank 100 may have a heating jacket 110 provided outside and filled with a thermal fluid so that the heating jacket 110 can heat the solution of the solution storage tank 100 up to 350° C. at maximum to dissolve the organic material in the organic solvent.

Besides, the solution storage tank 100 may further include an agitator 120 for uniformly mixing the organic solvent and the organic material together.

The ultrasonic diffuser 200 is a device provided in the solution storage tank 100 to apply ultrasonic wave to the organic material and grind/reduce the organic material into nanoparticles. The organic material is not easily dissolved just by heating and required to be forcedly ground to enhance the dissolution efficiency.

For reference, the ultrasonic diffuser has an oscillator, also called "generator", that changes the voltage having a frequency of 50 to 60 Hz into a high-frequency electric energy, and the high-frequency electric energy is converted into mechanical vibrations by piezoelectric ceramics in the converter, which is called "inverse piezoelectric effect". The vertical vibrations caused by the inverse piezoelectric effect are transferred to the liquid sample. The liquid sample is susceptible to expansion (negative pressure) and contraction (positive pressure) due to at least 20,000 vibrations per second and the constant amplitude of the probe (or tip) at which the ultrasonic vertical vibrations arrive in the liquid sample. Minute bubbles formed during this process break while the positive pressure is amplified. This phenomenon is called "cavitation", during which high-temperature and high-pressure instantaneous impulses having the pressure of about 1,000 bar and the instantaneous temperature of about 5,000 K generate and function as a source of very high energy to grind the organic material into particles.

The air compressor 300 serves to suction the solution in the solution storage tank 100 and transfer it to the next position, filter cartridge 400. During the transfer of the hot solution, the temperature of the solution lowers to precipitate the solution into crystals. In order to prevent this happening, it is necessary to transfer the solution under reduced pressure. For this purpose, an air compressor is suitably used. A pump may be used in place of the air compressor, but this also possibly causes a precipitation to form crystals. It is therefore preferable to use an air compressor unless a solution to the problem is provided.

The filter cartridge 400 consists of a filter case 410 and a filter material 420 filled in the filter case 410. The filter material may include at least one selected from the group consisting of metal oxide, active alumina, silica, titanium oxide, and natural stone, such as active carbon, bentonite, acid clay, and diatomite, which are used alone or in combination of at least two.

The temperature control device 500 is to raise the temperature of the filter cartridge 400 and prevent precipitation of crystals from the solution. The temperature control device 500 includes a casing 510 in which the filter cartridge 400 is mounted, a thermal fluid 520 filled in the casing 510, and a heater 530 for heating the thermal fluid 520.

The continuous reactor 600 receives the solution passing through the filter cartridge 400 and an anti-solvent stored in an anti-solvent storage tank 10 by a pump p and agitates the solution and the anti-solvent to produce a reactant having uniform particles. The continuous reactor 600 includes a cylinder 610, a thermal fluid chamber 620, a partition panel 630, a temperature control member 640, an agitating body 650, an agitating motor 660, a belt pulley 670, and a belt 671.

The cylinder 610 of the continuous reactor 600 has a reaction chamber 611 provided inside to receive the filtered solution and the anti-solvent. An anti-solvent inlet port 611a is provided on the one top side of the cylinder 610 to feed the anti-solvent into the reaction chamber 611, and a solution inlet port 611b is provided on the one bottom side of the cylinder 610 to feed the solution of the organic material. Reference number 611c (unexplained) denotes an outlet port through which the reactant after completion of the reaction is discharged.

The thermal fluid chamber 620 is provided in the shape of a ring on the outer side of the reaction chamber 611 and filled with a thermal fluid for regulating the temperature of the solution and the anti-solvent in the reaction chamber.

In this regard, the thermal fluid chamber 620 is divided into a plurality of thermal fluid chambers by the partition panel 630, which consists of an insulating material to prevent a heat exchange of the thermal fluids filled in the plural thermal fluid chambers 620.

Accordingly, heating the thermal fluid in each of the plural thermal fluid chambers 620 partitioned by the partition panel 630 at a different temperature creates a temperature gradient to the solution passing through the reaction chamber 611. The temperature gradient may vary depending on the temperature range of the thermal fluid.

Further, each thermal fluid chamber 620 may further include a temperature sensor 621 for sensing the temperature of the thermal fluid in each thermal fluid chamber and sending temperature data to the analyzer and compensator module 900.

The temperature control member 640 serves to control the temperature of the thermal fluid. For example, a circulator or a heater may be used as the temperature control member 640.

The agitating body 650 is of a rod shape and provided to be rotatable in the cylinder 610. The agitating body 650 serves to agitate the solution and the anti-solvent in the cylinder 610. As the agitating body 650 rotates, the mixing of fluids in the direction of the agitating body 650 decreases and the radial mixing of fluids increases. When the flow of fluids in the direction of the agitating body 650 exists, mixing of fluids in the cells occurs, and the fluids close to the agitating body 650 is fixed by the centrifugal force and tends to move in the direction of the inner wall of the cylinder 100. An unsteady flow form a pair of rings rotating in the opposite direction to each other along the direction of the agitating body 650, that is, Taylor vortex flows, which change the rotational speed of the agitating body 650 to readily cause turbulent flows and use the fluid stability.

The agitating motor 660 is arranged in the bottom portion of the cylinder 610 to provide a rotation power for the agitating body 650. The agitating motor 660 uses a speed-variable agitating motor capable of regulating the rotational speed in the range of 10 to 2,000 rpm by way of a DC voltage regulator (not shown). In this manner, the rotational speed of the agitating body 650 can be changed in the above-defined range (10 to 2,000 rpm), which leads to creation of turbulence in the solution.

The agitating motor 660 and the agitating body 650 are indirectly connected to each other via the belt pulley 670 and the belt 671. As the high internal temperature of the cylinder 610 is transferred to the agitating body 650, the agitating body 650 is maintained at high temperature. A direct transfer of the high heat to the agitating motor 660 can shorten the lifespan of the agitating motor 660. It is therefore possible to prevent a heat transfer by providing an indirect connection between the agitating body 650 and the agitating motor 660 via the belt 671 as described above. Although the connection via the belt 671 is given as an example in the above description, it is not intended to limit the present invention and, of course, a connection via a chain or a gear is also available.

On the other hand, the walls of the reaction chamber 611 and the thermal fluid chamber 620 may be coated with Teflon or made of hastelloy-C in order to provide corrosion resistance. Hastelloy-C, which is a HCl-resistant alloy with high corrosion resistance, may solve the problem in regards to corrosion resistance when used for such a portion as the cylinder 610 of the present invention that frequently gets in contact with the chemical solutions.

The organic material separator 700 is connected to the outlet port 611c of the continuous reactor 600 to divide the slurry-like reactant discharged from the continuous reactor 600 into a solid organic material and a filtrate.

The organic material storage tank 800 serves to store the solid organic material isolated by the organic material separator 700.

The analyzer and compensator module 900 collects a liquid isolated by the organic material separator 700, analyzes the liquid to determine whether it is in the normal state or not, and performs compensation to an optimal condition according to the analyzed data. The compensation function may be controlled by a computer.

Example 2

Hereinafter, a description will be given as to an apparatus that includes a dehydrator and a dryer for purification of tryptophan in addition to the above-specified components, such as the continuous reactor, the storage tank, the agitator, the diffuser, and the heating jacket.

The purification apparatus for purifying tryptophan includes, as shown in FIG. 4, a solid filter 10, a storage tank 20, a heating jacket 30, an air compressor 40, a continuous reactor 50, a dehydrator 60, and a dryer 70.

The solid filter 10 filters out the solid matter from a tryptophan solution and allows the solution to pass through. In this regard, the solid filter 10 has a mesh (or pore) size of 0.1 µm or greater, preferably 0.1 to 0.5 µm so as to filter out all the solids 0.5 µm or larger in size from the tryptophan solution and allow only the minute solids having a size of less than 0.5 µm to pass through. Consequently, the first purification step is performed. The storage tank 20 has a function of storing the tryptophan solution passed through the solid filter 10. At this, the storage tank 20 includes a temperature sensor 21 for sensing the temperature of the tryptophan solution stored in the storage tank 20 in real time.

The heating jacket 30 is provided outside the storage tank 20 to control the internal temperature of the storage tank 20. The heating jacket 30, which is filled with a thermal fluid, is disposed to immerse a part of the storage tank 20 and heat the thermal fluid by a heat source so that the tryptophan solution in the storage tank 20 can be controlled to have an appropriate temperature.

The air compressor 40 has a function of suctioning the tryptophan solution in the storage tank 20 and transferring it to the next position. A pump may be used in place of the air compressor.

The continuous reactor 50 receives the tryptophan solution transferred by the air compressor 40 and sulfuric acid transferred through a separate passage and agitates the solutions to continuously produce a reactant.

The continuous reactor is as defined above and its construction will not be separately described any more.

The dehydrator 60 is connected to the outlet port of the continuous reactor 50 to separate a filtrate from the slurry-like reactant discharged from the continuous reactor 50. A centrifugal separator may be used for the dehydrator 60.

Example 3

The tryptophan purification method disclosed in the present invention has the following procedures (Refer to FIG. 5).

First Step: Solid Removal Step S10.

The solid removal step is passing the tryptophan solution through the solid filter before storing it in the storage tank to eliminate solids of a predetermined size or greater. In this regard, the filter used in the solid removal step preferably has a mesh (or pore) size of 0.1 to 0.5 μm. Thus, the dissolved solids 0.5 μm or larger in size are filtered out from the tryptophan solution, so the tryptophan solution contains minute solids having a size of less than 0.5 μm.

Second Step: pH Adjusting Step S20.

The pH adjusting step S20 is adding NaOH (caustic soda) into the storage tank to adjust the pH value of the tryptophan solution. In this regard, the pH value of the tryptophan solution is preferably in the range of 11 to 3.

Third Step: Temperature Control Step S30.

The temperature control step S30 is providing the heating jacket outside the storage tank to maintain the tryptophan solution in the solution storage tank at a constant temperature.

Fourth Step: Density Enhancing Step S40.

The density enhancing step S40 is adding a polymer material to the tryptophan solution in the storage tank to enhance the particle density of the tryptophan solution. This step involves using the continuous reactor.

In this regard, the polymer material may be any one selected from polyvinyl alcohol (PVA), Carrageenan, alginic acid, HPC, or gelatin. As can be seen from FIG. 4, for example, large crystals are observed in the tryptophan solution with an elapse of time in either case of using PVA or gelatin. The tryptophan crystals using the polymer material have the higher growth rate than those not using the polymer material. The tryptophan crystals grow larger with an increase in the content of the acid solution (especially, sulfuric acid), which will be described in the sixth step.

Due to the addition of the polymer material, the particles of the tryptophan solution grow to a size of about 300 μm or greater. In this case, the use of sonication leads to the reduced strength of the particles to make the particles fragile. But, the strength of the particles can be enhanced when the polymer material is controlled to have a lower molecular weight.

Fifth Step: Feeding Step S50.

The feeding step S50 is feeding the tryptophan solution of the storage tank into the continuous reactor. The feeding process may be carried out automatically by way of an air compressor or the like. The construction of the continuous reactor will be described later.

Sixth Step: Crystal Precipitation Step S60.

The crystal precipitation step S60 is the process of adding an acid solution (especially, sulfuric acid) to the tryptophan solution fed into the continuous reactor to neutralize the pH value of the tryptophan solution and precipitate particulate crystals.

In other words, the tryptophan solution is an amphoteric substance very soluble in an acid solution or an alkaline solution. After dissolving the tryptophan solution in the acid solution or the alkaline solution, the opposite solution (i.e., an alkaline solution or an acid solution) is added (for example, an acid solution is added after the tryptophan solution is dissolved in a NaOH solution), to neutralize the pH value of the tryptophan solution and precipitate crystals.

Seventh Step: Solid-Liquid Separation Step S70.

The solid-liquid separation step S70 is a process of dehydrating the precipitated particulate crystals of the continuous reactor with the dehydrator to perform a solid-liquid separation.

In other words, the solid-liquid separation step S70 is adding the tryptophan crystals obtained with high water content into a centrifugal dehydrator to lower the water content to 60% or less. In order to calculate the proper dehydration time, dehydration is performed for a predetermined time, and the dehydrated sludge-like tryptophan crystals are collected and measured in regards to the water content with a water content measurer. According to the measurement results, there is a need for a process to increase or decrease the dehydration time.

In the preferred embodiment as achieved in the above procedures, the rotational speed of the dehydrator is 5,000 to 12,000 rpm and the dehydration time is 50 to 60 minutes. If the dehydrator is rotated at a low speed less than 500 rpm, the dehydration time becomes too long. If the rotational speed of the dehydrator is higher than 12,000 rpm, there is no significant difference in the dehydration rate from the case of rotating the dehydrator at the lower rotational speed, thus ending up with deteriorated dehydration efficiency.

Eighth Step: Drying Step S80.

In the drying step S80, the tryptophan sludge cake, which still has a high water content even after the completion of dehydration, needs to be dried with hot air into powder having a reduced water content of 10% or less. In this regard, it is possible to add a process of washing the sludge cake and eliminating the washing water using a centrifugal separator, before drying the sludge cake with hot air. Such a pulverizing process leads to a yield of tryptophan with high purity.

Experiment 1

Change of $H_2SO_4$ Feeding Rate
(Experiment Conditions)
Tryptophan concentration: 200 g/L
NaOH concentration: 5 mol/L
Initial pH: 14
$H_2SO_4$ concentration: 30%
Agitation rate: 300 rpm
Reaction temperature: 25° C.
$H_2SO_4$ feeding rate: 0.5 mL/min, 2 mL/min, all at once.
(Experimental Results)

It can be seen that the particle size of crystals decreases with an increase in the $H_2SO_4$ feeding rate. It is necessary to shorten the reaction time, because the particle size decreases with an increase in the reaction time.

TABLE 1

| | Particle size | | Cloud point | | |
|---|---|---|---|---|---|
| | PSA (μm) | Microscopy (μm) | Time | pH | Final pH |
| 1 | 48.64 | 40-45 | Immediate | — | 7.6 |
| 2 | 31 | 20-30 | 37 min | 9.26 | 7.7 |
| 3 | 12.49 | 10-20 | 110 min | 10.3 | 7.6 |

For reference, FIGS. 6, 7 and 8 are microscopic images of the cases 1, 2 and 3 of Table 1, respectively.

Experiment 2

Determination of Reaction Time
(Experiment Conditions)
Tryptophan concentration: 100 g/L
NaOH concentration: 5 mol/L
Initial pH: 14
$H_2SO_4$ concentration: 30%
Agitation rate: 300 rpm
Reaction temperature: 25° C.
$H_2SO_4$ feeding amount and rate: 100 mL & 16.7 mL/min
Other conditions: neutralize until pH 7 and then agitate for long time
(Experimental Results)
Although this experiment shows that tryptophan crystals with large particle size can be produced only when the reaction time is short, a short agitation time leads to production of small crystals having weak bonds and thus being easily broken. As shown in FIGS. 9 and 10 to 13, it is a tendency that the longer reaction time results in the lower yield of medium-sized crystals but the higher yield of large-sized crystals. However, the particle size distribution is uniform when the reaction time is about 18 times or less.

The recovery rate is about 95% or greater without a significant change depending on the reaction time, which shows that the tryptophan is precipitated in a short time.

Experiment 3

Change of Tryptophan Concentration
(Experiment Conditions)
NaOH concentration: 5 mol/L
Tryptophan concentration: 10, 100, 200 g/L
$H_2SO_4$ concentration: 30%
Agitation rate: 100, 300 rpm
Reaction temperature: 25° C.
pH: 7
Reaction time: 6 hrs
(Experimental Results)
As shown in FIG. 14, the particle size increases with a decrease in the tryptophan concentration. As shown in FIG. 15, the purity is about 99% or greater in all conditions. As shown in FIG. 16, the recovery rate is about 75% in all conditions. Reducing the dissolved tryptophan concentration is one of the methods to inhibit nucleation, and this method proves to be appropriate. It is considered that as the nucleation occurs less, tryptophan sticks to the nuclei to grow into crystals.

Experiment 4

Change of Agitation Rate
(Experiment Conditions)
NaOH concentration: 5 mol/L
Tryptophan concentration: 10 g/L
$H_2SO_4$ concentration: 30%
Agitation rate: 100, 300 rpm
Reaction temperature: 25° C.
pH: 7
Reaction time: 6 hrs
(Experimental Results)
As shown in FIGS. 17, 18 and 19, the particle size increases with the reduced agitation rate. This material is a plate-shaped substance with the weak bonding strength of particles. The analytic results show that the crystals form to be easily broken as the plate is only 1 μm or less in height.

What is claimed is:

1. A purification apparatus comprising:
   a solution storage tank to store a solution;
   an ultrasonic diffuser to diffuse particles contained in the solution of the solution storage tank with an ultrasonic wave;
   an agitator to agitate the solution stored in the solution storage tank;
   a heating jacket provided outside the solution storage tank to control an internal temperature of the solution storage tank;
   an air compressor to suction and transfer the solution of the solution storage tank; and
   a reactor to receive the solution transferred by the air compressor and a solvent transferred through a separate passage, and to agitate the solution to continuously produce a reactant having uniform particles; wherein the reactor comprises:
   a cylinder having a reaction chamber inside therein, an anti-solvent inlet port provided on one top side of the cylinder to feed the anti-solvent into the reaction chamber, and a solution inlet port provided on one bottom side of the cylinder to feed the solution into the reaction chamber;
   a thermal fluid chamber provided in a shape of a ring on an outer side of the reaction chamber and filled with a thermal fluid to regulate a temperature of the solution and the anti-solvent in the reaction chamber;
   a partition panel provided to divide a space of the thermal fluid chamber into a plurality of fluid chambers and formed of an insulating material to prevent heat exchange of the thermal fluids filled in said plurality of fluid chambers;
   a temperature control member to control a temperature of the thermal fluid filled in each fluid chamber;
   an agitating body configured to be rotatable in the cylinder and to agitate the solution and the anti-solvent in the cylinder;
   an agitating motor arranged in a bottom portion of the cylinder; and
   a belt pulley and a belt connecting an axis of the agitating motor to one end of the agitating body to transfer a driving force of the agitating motor to the agitating body.

2. The purification apparatus as claimed in claim 1, wherein the reactor further comprises a temperature sensor to sense the temperature of the thermal fluid in each fluid chamber and to send temperature data to the analyzer and compensator module.

3. The purification apparatus as claimed in claim 1, wherein the reaction chamber and the thermal fluid chamber have walls coated with Teflon or formed of hastelloy-C to provide corrosion resistance.

4. A purification apparatus comprising:
   a solution storage tank to store a solution;
   an ultrasonic diffuser to diffuse particles contained in the solution of the solution storage tank with an ultrasonic wave;
   an agitator to agitate the solution stored in the solution storage tank;
   a heating jacket provided outside the solution storage tank to control an internal temperature of the solution storage tank;
   an air compressor to suction and transfer the solution of the solution storage tank;

a filter cartridge to filter out minute impurities contained in the solution transferred by the air compressor;

a temperature control device comprising a casing to receive the filter cartridge, a thermal fluid filled in the casing, and a heater to heat the thermal fluid;

a reactor to receive the solution passing through the filter cartridge and an anti-solvent stored in an anti-solvent storage tank, and to agitate the solution and the anti-solvent to produce a reactant having uniform particles;

an organic material separator connected to an output port of the reactor to divide a slurry-like reactant discharged from the reactor into an organic material and a filtrate;

an organic material storage tank to store the organic material in a solid state isolated by the organic material separator; and an analyzer and compensator module to collect and analyze a liquid isolated by the organic material separator to provide analyzed data, and to perform compensation according to the analyzed data.

5. The purification apparatus as claimed in claim 4, wherein the filter cartridge comprises a filter case filled with a filter material comprising at least one material selected from a group consisting of metal oxide, active alumina, silica, titanium oxide, active carbon, bentonite, acid clay, and diatomite.

6. The purification apparatus as claimed in claim 4, wherein the organic material separator is a centrifugal separator or a dehydrator.

7. The purification apparatus as claimed in claim 4, wherein the reactor comprises:
    a cylinder having a reaction chamber inside therein, an anti-solvent inlet port provided on one top side of the cylinder to feed the anti-solvent into the reaction chamber, and a solution inlet port provided on one bottom side of the cylinder to feed the solution into the reaction chamber;
    a thermal fluid chamber provided in a shape of a ring on an outer side of the reaction chamber and filled with a thermal fluid to regulate a temperature of the solution and the anti-solvent in the reaction chamber;
    a partition panel provided to divide a space of the thermal fluid chamber into a plurality of fluid chambers and formed of an insulating material to prevent heat exchange of the thermal fluids filled in said plurality of fluid chambers;
    a temperature control member to control a temperature of the thermal fluid filled in each fluid chamber;
    an agitating body configured to be rotatable in the cylinder and to agitate the solution and the anti-solvent in the cylinder;
    an agitating motor arranged in a bottom portion of the cylinder; and
    a belt pulley and a belt connecting an axis of the agitating motor to one end of the agitating body to transfer a driving force of the agitating motor to the agitating body.

8. The purification apparatus as claimed in claim 7, wherein the reactor further comprises a temperature sensor to sense the temperature of the thermal fluid in each fluid chamber and to send temperature data to the analyzer and compensator module.

9. The purification apparatus as claimed in claim 7, wherein the reaction chamber and the thermal fluid chamber have walls coated with Teflon or formed of hastelloy-C to provide corrosion resistance.

10. A tryptophan purification method using a purification apparatus of claim 4, the method comprising the steps of:
    passing a tryptophan solution through a solid filter before storing the tryptophan solution in the solution storage tank of the purification apparatus to eliminate solid matter of a predetermined size or greater;
    adding NaOH into the solution storage tank to adjust a pH value of the tryptophan solution;
    providing the heating jacket outside the solution storage tank to maintain a temperature of the tryptophan solution in the solution storage tank at a constant level;
    adding a polymer material to the tryptophan solution in the solution storage tank to enhance a particle density of the tryptophan solution;
    feeding the tryptophan solution of the solution storage tank into the reactor of the purification apparatus;
    adding an acid solution to the tryptophan solution fed into the reactor to neutralize the pH value of the tryptophan solution and precipitate particulate crystals;
    performing a solid-liquid separation on the precipitated particulate crystals with the organic material separator; and
    hot-air drying a solid component separated by the organic material separator.

11. A purification apparatus comprising:
    a solid filter to filter out solid matter from a solution and to separate the solution;
    a solution storage tank to store the solution passed through the solid filter;
    an ultrasonic diffuser to diffuse particles contained in the solution of the solution storage tank with an ultrasonic wave;
    an agitator to agitate the solution stored in the solution storage tank;
    a heating jacket provided outside the solution storage tank to control an internal temperature of the solution storage tank;
    an air compressor to suction and transfer a tryptophan solution of the solution storage tank;
    a reactor to receive the tryptophan solution transferred by the air compressor and a solvent transferred through a separate passage, and to agitate the tryptophan solution to continuously produce a reactant;
    a dehydrator connected to an outlet port of the reactor to separate a filtrate from a slurry-like reactant discharged from the reactor; and
    a dryer to dry a solid component separated by the dehydrator.

12. A tryptophan purification method using a purification apparatus of claim 11, comprising the steps of:
    passing a tryptophan solution through a solid filter before storing the tryptophan solution in a solution storage tank of the purification apparatus to eliminate solid matter of a predetermined size or greater;
    adding NaOH into the solution storage tank to adjust a pH value of the tryptophan solution;
    providing a heating jacket outside the solution storage tank to maintain a temperature of the tryptophan solution in the solution storage tank at a constant level;
    adding a polymer material to the tryptophan solution in the solution storage tank to enhance a particle density of the tryptophan solution;

feeding the tryptophan solution of the solution storage tank into a reactor of the purification apparatus;

adding an acid solution to the tryptophan solution fed into the reactor to neutralize the pH value of the tryptophan solution and precipitate particulate crystals;

dehydrating the precipitated particulate crystals with a dehydrator of the purification apparatus to perform a solid-liquid separation; and hot-air drying a solid component separated by the dehydrator.

13. A tryptophan purification method using a purification apparatus, comprising steps of:

wherein the purification apparatus comprises: a solution storage tank to store a solution; an ultrasonic diffuser to diffuse particles contained in the solution of the solution storage tank with an ultrasonic wave; an agitator to agitate the solution stored in the solution storage tank; a heating jacket provided outside the solution storage tank to control an internal temperature of the solution storage tank; an air compressor to suction and transfer the solution of the solution storage tank; and a reactor to receive the solution transferred by the air compressor and a solvent transferred through a separate passage, and to agitate the solution to continuously produce a reactant having uniform particles;

passing a tryptophan solution through a solid filter before storing the tryptophan solution in the solution storage tank of the purification apparatus to eliminate solid matter of a predetermined size or greater;

adding NaOH into the solution storage tank to adjust a pH value of the tryptophan solution;

providing the heating jacket outside the solution storage tank to maintain a temperature of the tryptophan solution in the solution storage tank at a constant level;

adding a polymer material to the tryptophan solution in the solution storage tank to enhance a particle density of the tryptophan solution;

feeding the tryptophan solution of the solution storage tank into the reactor of the purification apparatus;

adding an acid solution to the tryptophan solution fed into the reactor to neutralize the pH value of the tryptophan solution and precipitate particulate crystals;

dehydrating the precipitated particulate crystals with the dehydrator of the purification apparatus to perform a solid-liquid separation; and hot-air drying a solid component separated by the dehydrator.

* * * * *